US010076338B2

(12) United States Patent
Fitz et al.

(10) Patent No.: US 10,076,338 B2
(45) Date of Patent: Sep. 18, 2018

(54) DETACHABLE COIL INCORPORATING STRETCH RESISTANCE

(71) Applicant: MicroVention, Inc., Aliso Viejo, CA (US)

(72) Inventors: Matthew J. Fitz, Vista, CA (US); Cathy Lei, Chino Hills, CA (US); Joseph Gulachenski, Trabuco Canyon, CA (US); Maricruz Castaneda, Mission Viejo, CA (US); Gary Currie, Fallbrook, CA (US)

(73) Assignee: MicroVention, Inc., Aliso Viejo, CA (US)

(*) Notice: Subject to any disclaimer, the term of this patent is extended or adjusted under 35 U.S.C. 154(b) by 208 days.

(21) Appl. No.: 15/081,065

(22) Filed: Mar. 25, 2016

(65) Prior Publication Data
US 2016/0206322 A1    Jul. 21, 2016

Related U.S. Application Data

(63) Continuation of application No. 12/180,834, filed on Jul. 28, 2008.

(60) Provisional application No. 60/952,520, filed on Jul. 27, 2007.

(51) Int. Cl.
*A61F 2/06* (2013.01)
*A61B 17/12* (2006.01)
(Continued)

(52) U.S. Cl.
CPC .. *A61B 17/12154* (2013.01); *A61B 17/12022* (2013.01); *A61B 17/12145* (2013.01);
(Continued)

(58) Field of Classification Search
CPC ........ A61B 17/12022; A61B 17/12154; A61B 17/12145; A61B 17/12113;
(Continued)

(56) References Cited

U.S. PATENT DOCUMENTS 5,853,418 A    12/1998  Ken et al.
6,193,728 B1    2/2001  Ken et al.
(Continued)

FOREIGN PATENT DOCUMENTS

EP          1889577 A1    2/2008
WO    WO2005/113035 A2   12/2005
(Continued)

OTHER PUBLICATIONS

United States Patent and Trademark Office Patent Trial and Appeal Board, Decision on Appeal mailed Jan. 25, 2016 in U.S. Appl. No. 12/180,834, 7 pages.
(Continued)

*Primary Examiner* — Katherine M Shi

(57) ABSTRACT

An implantable embolic device having a stretch-resistant member passing therethrough that also serves as a tether for connecting the device to a delivery system. The stretch-resistant member is attached at a proximal and distal end of the device and extends proximally to the delivery device. The proximal attachment point serves to isolate a distal, stretch resisting segment of the member from axial tension placed on a proximal, connecting section of the member. Thus, the portion of the stretch-resistant member being used to connect the embolic device to a delivery device may be placed under tension without placing tension or distorting the implant.

10 Claims, 6 Drawing Sheets

(51) Int. Cl.
*A61F 2/95* (2013.01)
*A61F 2/01* (2006.01)
*A61B 90/00* (2016.01)

(52) U.S. Cl.
CPC ............... *A61F 2/95* (2013.01); *A61B 90/39* (2016.02); *A61B 2017/12068* (2013.01); *A61F 2002/011* (2013.01); *A61F 2002/9505* (2013.01)

(58) Field of Classification Search
CPC ...... A61B 2017/12068; A61B 17/1214; A61B 2017/12063; A61F 2/95
USPC .................. 606/108, 191, 194, 200; 623/1.11
See application file for complete search history.

(56) References Cited

U.S. PATENT DOCUMENTS

| 2004/0002733 | A1 | 1/2004 | Teoh |
| 2004/0034363 | A1 | 2/2004 | Wilson et al. |
| 2006/0052815 | A1 | 3/2006 | Fitz et al. |
| 2007/0239193 | A1 | 10/2007 | Simon et al. |
| 2008/0103585 | A1 | 5/2008 | Monstadt et al. |

FOREIGN PATENT DOCUMENTS

| WO | WO2005/113035 A3 | 12/2005 | |
| WO | WO 2006/126182 | * | 11/2006 |

OTHER PUBLICATIONS

United States Patent and Trademark Office, Final Office Action dated Nov. 7, 2012 in U.S. Appl. No. 12/180,834, 12 pages.
United States Patent and Trademark Office, Office Action dated Apr. 12, 2012 in U.S. Appl. No. 12/180,834, 10 pages.
United States Patent and Trademark Office, Final Office Action dated Jan. 6, 2011 in U.S. Appl. No. 12/180,834, 10 pages.
United States Patent and Trademark Office, Office Action dated Jun. 29, 2010 in U.S. Appl. No. 12/180,834, 14 pages.
WIPO, U.S. International Search Authority, International Search Report and Written Opinion dated Oct. 20, 2008 in International Patent Application No. PCT/US2008/071325, 9 pages.

* cited by examiner

*Direct Current (DC) Signaling*

*Alternating Current (AC) Signaling*

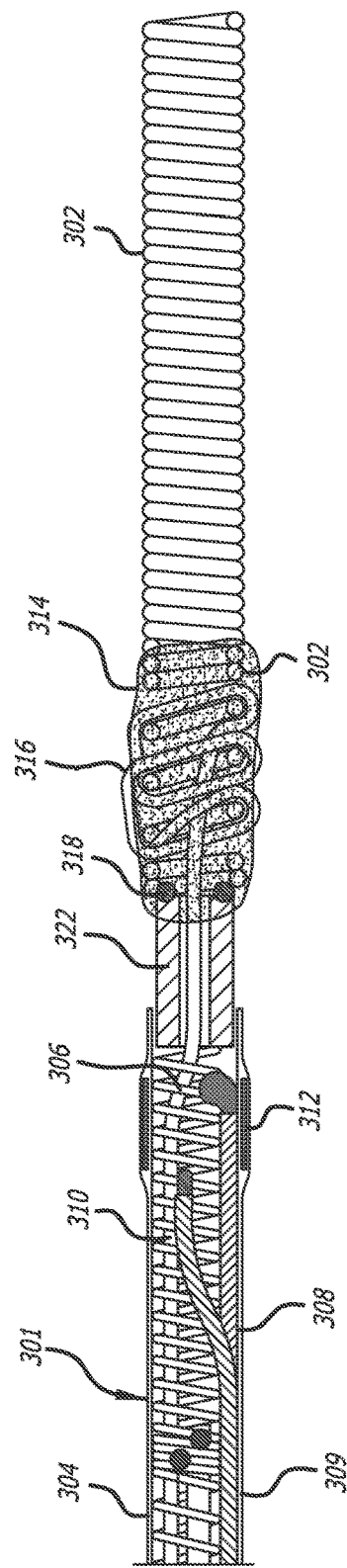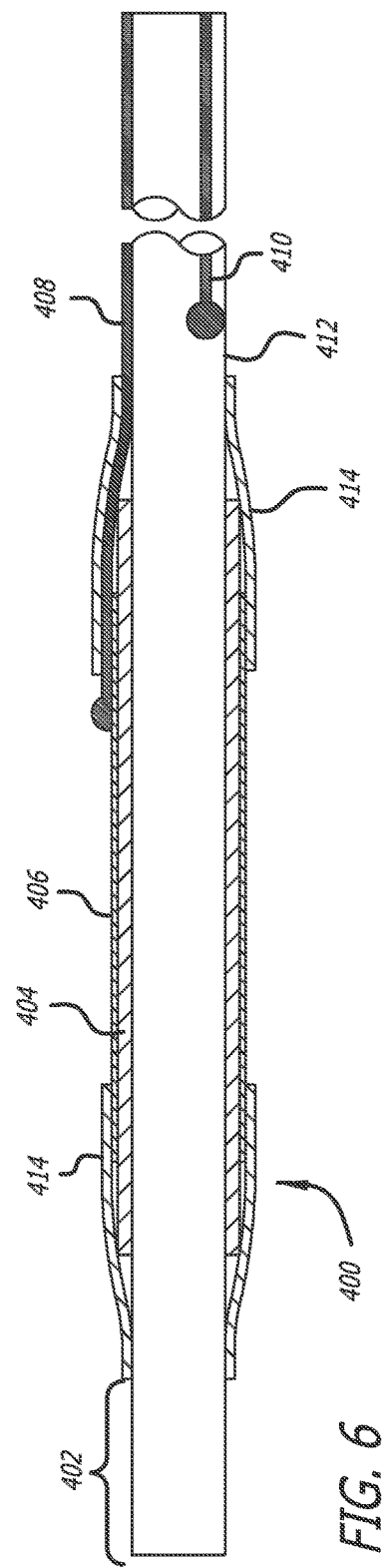

DETACHABLE COIL INCORPORATING STRETCH RESISTANCE

RELATED APPLICATIONS

This application is a continuation of and claims priority to U.S. patent application Ser. No. 12/180,834 filed Jul. 28, 2008, which claims priority to U.S. Provisional Application Ser. No. 60/952,520, filed Jul. 27, 2007, entitled Detachable Coil Incorporating Stretch Resistance, incorporated by reference herein. This application also incorporates by reference U.S. Provisional Application Ser. No. 60/604,671, filed Aug. 25, 2004 entitled Thermal Detachment System For Implantable Devices, U.S. Provisional Application Ser. No. 60/685,342 filed May 27, 2005 entitled Thermal Detachment System For Implantable Devices and U.S. patent application Ser. No. 11/212,830 filed Aug. 25, 2005 entitled Thermal Detachment System For Implantable Devices.

FIELD OF THE INVENTION

The present invention relates to systems and methods for delivering implant devices to a target site or location within the body of a patient. The present invention also relates to systems and methods for delivering a stretch-resistant implant and a method for attaching and detaching the implant to and from a delivery system.

BACKGROUND OF THE INVENTION

Delivery of implantable therapeutic devices by less invasive means has been demonstrated to be desirable in numerous clinical situations. For example, vascular embolization has been used to control vascular bleeding, to occlude the blood supply to tumors, to occlude fallopian tubes, and to occlude vascular aneurysms, particularly intracranial aneurysms. In recent years, vascular embolization for the treatment of aneurysms has received much attention. Implants used to treat aneurysms are often convoluted or coiled lengths of wound wire and are referred to as "microcoils." Microcoils work by filling an aneurysm causing the blood-flow through the aneurysm to slow or stop, thereby inducing thrombosis within the aneurysm.

Microcoils are extremely flexible and have very little structural integrity. In order to make them easier to retrieve and reposition, recent efforts have been directed to making them stretch-resistant. For example, a stretch-resistant embolic coil having a stretch-resistant member passing through the interior lumen of the coil is described in U.S. Pat. No. 5,582,619 to Ken. US Patent Publication No. 2004/0034363 to Wilson also discloses an embolic coil with a stretch resistant member having a distal end attached near the distal end of the coil and a proximal end of the member attached to a delivery catheter.

Several different treatment modalities have been employed in the prior art for deploying implant devices. For example, numerous repositionable detachment systems for implant devices have been described in the prior art including U.S. Pat. No. 5,895,385 to Guglielmi et al. and U.S. Pat. No. 5,108,407 to Geremia et al., the contents of which are hereby incorporated by reference. Several systems, such as those disclosed in U.S. Pat. No. 6,500,149 to Gandhi et al. and U.S. Pat. No. 4,346,712 to Handa et al., the contents of which are hereby incorporated by reference, describe the use of a heater to detach and deploy the implant device.

SUMMARY OF THE INVENTION

The present invention is an implant delivery and detachment system used to position and deploy implantable devices such as coils, stents, filters, and the like within a body cavity including, but not limited to, blood vessels, fallopian tubes, malformations such as fistula and aneurysms, heart defects (e.g. left atrial appendages and sepal openings), and other luminal organs.

The system comprises an implant, a delivery catheter (generically referred to as the pusher or delivery pusher), a detachable joint for coupling the implant to the pusher, a heat generating apparatus (generically referred to as the heater), and a power source to apply energy to the heater.

The present invention also includes an apparatus for delivering a stretch-resistant embolic coil and a method for attaching and detaching the coil to a delivery system. The apparatus incorporates a coil and a stretch-resistant member with a distal end and a proximal end. In addition to providing stretch resistance, the member serves to detachably couple the implant coil to the delivery catheter.

The present invention may also be used in conjunction with the delivery mechanism disclosed in U.S. patent application Ser. No. 11/212,830 filed Aug. 25, 2005 entitled "Thermal detachment system for implanting devices," which is incorporated by reference herein in its entirety.

In one aspect of the present invention, the implant is coupled to the pusher using a tether, string, thread, wire, filament, fiber, or the like. Generically this is referred to as the tether. The tether may be in the form of a monofilament, rod, ribbon, hollow tube, or the like.

Many materials can be used to detachably join the implant to the pusher. One class of materials are polymers such as polyolefin, polyolefin elastomer such as those made by Dow marketed under the trade name Engage or Exxon marketed under the trade name Affinity, polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials is metals such as nickel titanium alloy (Nitinol), gold, and steel. The selection of the material depends on the capacity of the material to store potential energy, the melting or softening temperature, the power used for detachment, and the body treatment site.

The tether may be joined to the implant and/or the pusher by welding, knot tying, soldering, adhesive bonding, or other means known in the art. In one embodiment where the implant is a coil, the tether may run through the inside lumen of the coil and be attached to the distal end of the coil. This design not only joins the implant to the pusher, but also imparts stretch resistance to the coil without the use of a secondary stretch resistant member. In other embodiments where the implant is a coil, stent, or filter; the tether is attached to the proximal end of the implant.

In another aspect of the present invention, the tether detachably coupling the implant to the pusher acts as a reservoir of potential energy that is released during detachment. This advantageously lowers the time and energy required to detach the implant because it allows the tether to be severed by application of heat without necessarily fully melting the material. The stored energy also may exert a force on the implant that pushes it away from the delivery catheter. This separation tends to make the system more reliable because it may prevent the tether from re-solidifying and holding the implant after detachment.

Stored energy may be imparted in several ways. In one embodiment, a spring is disposed between the implant and pusher. The spring is compressed when the implant is attached to the pusher by joining one end of the tether to one of either the pusher or implant, pulling the free end of the tether until the spring is at least partially compressed, then affixing the free end of the tether to the other of the implant or the pusher. Since both ends of the tether are restrained, potential energy in the form of tension on the tether (or compression in the spring) is stored within the system.

In another embodiment, one end of the tether is fixed as in the previous embodiment, and then the tether is placed in tension by pulling on the free end of the tether with a pre-determined force or displacement. When the free end of the tether is then affixed, the elongation (i.e. elastic deformation) of the tether material itself stores energy.

In another aspect of the present invention, a heater is disposed on or within the pusher, typically, but not necessarily, near the distal end of the pusher. The heater may be attached to the pusher by, for example, soldering, welding, adhesive bonding, mechanical boding, or other techniques known in the art. The heater may be in the form of a wound coil, heat pipe, hollow tube, band, hypotube, solid bar, toroid, or similar shape. The heater may be made from a variety of materials such as steel, chromium cobalt alloy, platinum, silver, gold, tantalum, tungsten, mangalin, chromium nickel alloy available from California Fine Wire Company under the trade name Stable Ohm, conductive polymer, or the like. The tether is disposed in proximity to the heater. The tether may pass through the lumen of a hollow or coil-type heater or may be wrapped around the heater. Although the tether may be disposed in direct contact with the heater, this is not necessary. For ease of assembly, the tether may be disposed be in proximity to, but not actually touching, the heater.

The delivery catheter or pusher is an elongate member with distal and proximal ends adapted to allow the implant to be maneuvered to the treatment site. The pusher comprises a core mandrel and one or more electrical leads to supply power to the heater. The pusher may taper in dimension and/or stiffness along the length, with the distal end usually being more flexible than the proximal end. In one embodiment, the pusher is adapted to be telescopically disposed within a delivery conduit such as a guide catheter or microcatheter. In another embodiment, the pusher contains an inner lumen allowing it to be maneuvered over a guide wire. In still another embodiment, the pusher can be maneuvered directly to the treatment site without a secondary device. The pusher may have a radiopaque marking system visible with fluoroscopy that allows it to be used in conjunction with radiopaque markings on the microcatheter or other adjunctive devices.

In another aspect of the present invention, the core mandrel is in the form of a solid or hollow shaft, wire, tube, hypotube, coil, ribbon, or combination thereof. The core mandrel may be made from plastic materials such as PEEK, acrylic, polyamide, polyimide, Teflon, acrylic, polyester, block copolymer such as PEBAX, or the like. The plastic member(s) may be selectively stiffened along the length with reinforcing fibers or wires made from metal, glass, carbon fiber, braid, coils, or the like. Alternatively, or in combination with plastic components, metallic materials such as stainless steel, tungsten, chromium cobalt alloy, silver, copper, gold, platinum, titanium, nickel titanium alloy (Nitinol), and the like may be used to form the core mandrel. Alternatively, or in combination with plastic and/or metallic components, ceramic components such as glass, optical fiber, zirconium, or the like may be used to form the core mandrel. The core mandrel may also be a composite of materials.

In one embodiment, the core mandrel comprises an inner core of radiopaque material such as platinum or tantalum and an outer covering of kink-resistant material such as steel or chromium cobalt. By selectively varying the thickness of the inner core, radiopaque identifiers can be provided on the pusher without using secondary markers.

In another embodiment, a core material, for example stainless steel, with desirable material properties such as kink resistance and/or compressive strength is selectively covered (by, for example, plating, drawing, or similar methods known in the art) with a low electrical resistance material such as copper, aluminum, gold, or silver to enhance its electrical conductivity, thus allowing the core mandrel to be used as an electrical conductor.

In another embodiment, a core material, for example, glass or optical fiber, with desirable properties such as compatibility with Magnetic Resonance Imaging (MRI), is covered with a plastic material such as PEBAX or polyimide to prevent the glass from fracturing or kinking.

In another aspect of the present invention, the heater is attached to the pusher, and then one or more electrical conductors are attached to the heater. In one embodiment a pair of conductive wires runs substantially the length of the pusher and is coupled to the heater near the distal end of the pusher and to electrical connectors near the proximal end of the pusher. In another embodiment, one conductive wire runs the substantially the length of the pusher and the core mandrel itself is made from a conductive material or coated with a conductive material to act as a second electrical lead. The wire and the mandrel are coupled to the heater near the distal end and to one or more connectors near the proximal end of the pusher. In another embodiment, a bipolar conductor is coupled to the heater and is used in conjunction with radiofrequency (RF) energy to power the heater. In any of the embodiments, the conductor(s) may run in parallel to the core mandrel or may pass through the inner lumen of a substantially hollow core mandrel (for example, a hypotube).

In another aspect of the present invention, an electrical and/or thermally insulating cover or sleeve may be placed over the heater. The sleeve may be made from insulating materials such as polyester (PET), Teflon, block copolymer, silicone, polyimide, polyamide, and the like.

In another aspect of the present invention, electrical connector(s) are disposed near the proximal end of the pusher so that the heater can be electrically connected to a power source through the conductors. In one embodiment, the connectors are in the form of a plug with one or more male or female pins. In another embodiment, the connector(s) are tubes, pins, or foil that can be connected with clip-type connectors. In another embodiment, the connector(s) are tubes, pins, or foil that are adapted to mate with an external power supply.

In another aspect of the present invention, the pusher connects to an external power source so that the heater is electrically coupled to the power source. The power source may be from battery(s) or connected to the electrical grid by a wall outlet. The power source supplies current in the form of direct current (DC), alternating current (AC), modulated direct current, or radiofrequency (RF) at either high or low frequency. The power source may be a control box that operates outside of the sterile field or may be a hand-held device adapted to operate within a sterile field. The power source may be disposable, rechargeable, or may be reusable with disposable or rechargeable battery(s).

In another aspect of the present invention, the power source may comprise an electronic circuit that assists the user with detachment. In one embodiment, the circuit detects detachment of the implant and provides a signal to the user when detachment has occurred. In another embodiment, the circuit comprises a timer that provides a signal to the user when a pre-set length of time has elapsed. In another embodiment, the circuit monitors the number of detachments and provides a signal or performs an operation such as locking the system off when a pre-set number of detachments have been performed. In another embodiment, the circuit comprises a feedback loop that monitors the number of attachment attempts and increases the current, voltage, and/or detachment time in order to increase the likelihood of a successful detachment.

In another aspect of the present invention, the construction of the system allows for extremely short detachment time. In one embodiment the detachment time is less than 1 second.

In another aspect of the present invention, the construction of the system minimizes the surface temperature of the device during detachment. In one embodiment, the surface temperature at the heater during detachment is under 50° C. In another embodiment, the surface temperature at the heater during detachment is under 42° C.

In another aspect of the present invention, the implant device includes both a stretch-resistant attribute and the ability to detachably couple the device to the delivery catheter. This aspect of the present invention advantageously reduces the number of components and assembly steps required to build a stretch-resistant implant device.

In another aspect of the present invention, tension is placed on a coupling portion of a stretch-resistant implant device while minimizing tension in a stretch-resistant portion of the same device. Thus, tension may be placed on the device as described in U.S. patent application Ser. No. 11/212,830 during attachment of the implant device to the delivery catheter without placing excessive tension, which might distort the shape of the implant device (e.g., embolic coil), on the portion of the implant device that provides stretch-resistance.

These and other aspects and features of the present invention will be appreciated upon consideration of the following drawings and detailed descriptions.

BRIEF DESCRIPTION OF THE DRAWINGS

FIG. 4 illustrates a cross-sectional side view of a third embodiment of a detachment system according to the present invention;

FIG. 6 illustrates a cross-sectional side view of an electrical connector of a detachment system according to the present invention;

DETAILED DESCRIPTION OF THE INVENTION

Figure 1:
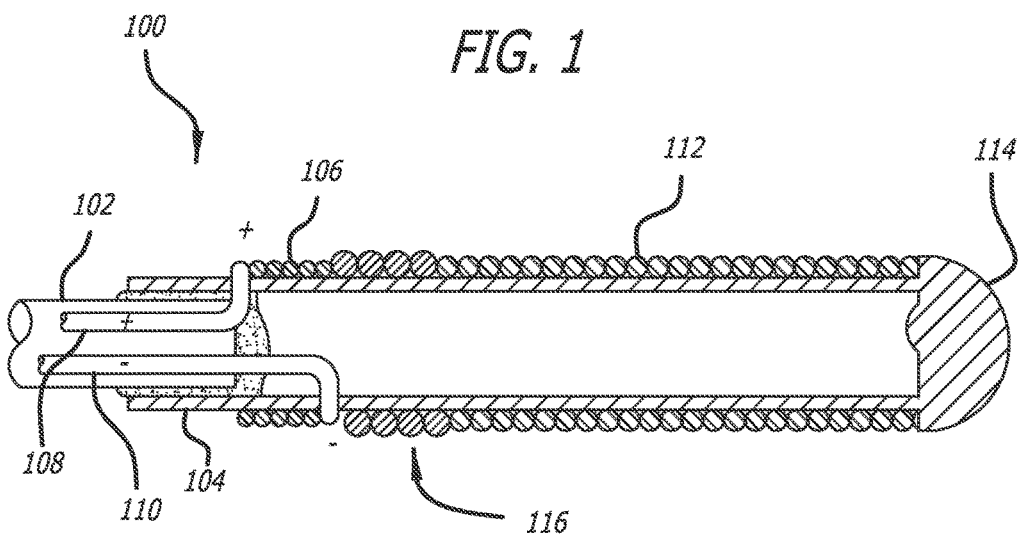
FIG. 1 illustrates a cross-sectional side view of a first embodiment of a detachment system according to the present invention.

Turning to FIG. 1, a detachment system 100 of the present invention, and specifically the distal portion of the detachment system 100, is illustrated. The detachment system 100 includes a pusher 102 that is preferably flexible. The pusher 102 is configured for use in advancing an implant device 112 into and within the body of a patient and, specifically, into a target cavity site for implantation and delivery of the implant device 112. Potential target cavity sites include but are not limited to blood vessels and vascular sites (e.g., aneurysms and fistula), heart openings and defects (e.g., the left atrial appendage), and other luminal organs (e.g., fallopian tubes).

A stretch-resistant tether 104 detachably couples the implant 112 to the pusher 102. In this example, the tether 104 is a plastic tube that is bonded to the pusher 102. A substantially solid cylinder could also be a design choice for the tether 104. The stretch resistant tether 104 extends at least partially through the interior lumen of an implant device 112.

Near the distal end of the pusher 102, a heater 106 is disposed in proximity to the stretch resistant tether 104. The heater 106 may be wrapped around the stretch resistant tether 104 such that the heater 106 is exposed to or otherwise in direct contact with the blood or the environment, or alternatively may be insulated by a sleeve, jacket, epoxy, adhesive, or the like. The pusher 102 comprises a pair of electrical wires, positive electrical wire 108 and negative electrical wire 110. The wires 108 and 110 are coupled to the heater 106 by any suitable means, such as, e.g., by welding or soldering.

The electrical wires 108, 110 are capable of being coupled to a source of electrical power (not shown). As illustrated the negative electrical wire 110 is coupled to the distal end of the heater 106 and the positive electrical wire 108 is coupled to the proximal end of the heater 106. In another embodiment, this configuration may be reversed, i.e., the negative electrical wire 110 is coupled to the proximal end of the heater 106 while the positive electrical wire 108 is coupled to the distal end of the heater 106.

Energy is applied to the heater 106 from the electrical wires 108, 110 in order to sever the portion of the tether 104 in the proximity of the heater 106. It is not necessary for the heater 106 to be in direct contact with the tether 104. The heater 106 merely should be in sufficient proximity to the tether 104 so that heat generated by the heater 106 causes the tether 104 to sever. As a result of activating the heater 106, the section of the stretch resistant tether 104 that is approximately distal from the heater 106 and within the lumen of an implant device 112 is released from the pusher 102 along with the implant device 112.

As illustrated, the implant device 112 is an embolic coil. An embolic coil suitable for use as the implant device 112 may comprise a suitable length of wire formed into a helical microcoil. The coil may be formed from a biocompatible material including platinum, rhodium, palladium, rhenium, tungsten, gold, silver, tantalum, and various alloys of these metals, as well as various surgical grade stainless steels. Specific materials include the platinum/tungsten alloy known as Platinum 479 (92% Pt, 8% W, available from Sigmund Cohn, of Mount Vernon, N.Y.) and nickel/titanium alloys (such as the nickel/titanium alloy known as Nitinol).

Another material that may be advantageous for forming the coil is a bimetallic wire comprising a highly elastic metal with a highly radiopaque metal. Such a bimetallic wire would also be resistant to permanent deformation. An example of such a bimetallic wire is a product comprising a Nitinol outer layer and an inner core of pure reference grade platinum, available from Sigmund Cohn, of Mount Vernon, N.Y., and Anomet Products, of Shrewsbury, Mass.

Commonly-assigned U.S. Pat. No. 6,605,101 provides a further description of embolic coils suitable for use as the implant device 112, including coils with primary and secondary configurations wherein the secondary configuration minimizes the degree of undesired compaction of the coil after deployment. The disclosure of U.S. Pat. No. 6,605,101 is fully incorporated herein by reference. Furthermore, the implant device 112 may optionally be coated or covered with a hydrogel or a bioactive coating known in the art.

The coil-type implant device 112 resists unwinding because the stretch resistant tether 104 that extends through the lumen of the implant device 112 requires substantially more force to plastically deform than the implant device 112 itself. The stretch resistant tether 104 therefore assists in preventing the implant device 112 from unwinding in situations in which the implant device 112 would otherwise unwind.

During assembly, potential energy may be stored within the device to facilitate detachment. In one embodiment, an optional spring 116 is placed between the heater 106 and the implant device 112. The spring is compressed during assembly and the distal end of the tether 104 may be tied or coupled to the distal end of the implant device 112, or may be melted or otherwise formed into an atraumatic distal end 114.

In one embodiment, the stretch resistant tether 104 is made from a material such as a polyolefin elastomer, polyethylene, or polypropylene. One end of the tether 104 is attached to the pusher 102 and the free end of the tether 104 is pulled through the implant 112 with the proximal end of the implant 112 flush to either the heater 106 (if no spring 116 is present) or to the compressed spring 116. A pre-set force or displacement is used to pre-tension the tether 104, thus storing energy in an axial orientation (i.e. co-linear or parallel to the long axis of the pusher 102) within the tether 104. The force or displacement depends on the tether material properties, the length of the tether 104 (which itself depends on the tether's attachment point on the pusher and the length of the implant). Generally, the force is below the elastic limit of the tether material, but sufficient to cause the tether to sever quickly when heat is applied. In one preferred embodiment wherein the implant to be deployed is a cerebral coil, the tether has a diameter within the range of approximately 0.001 to 0.007 inches. Of course the size of the tether can be changed to accommodate different types and sizes of other implants as necessary.

Figure 2:
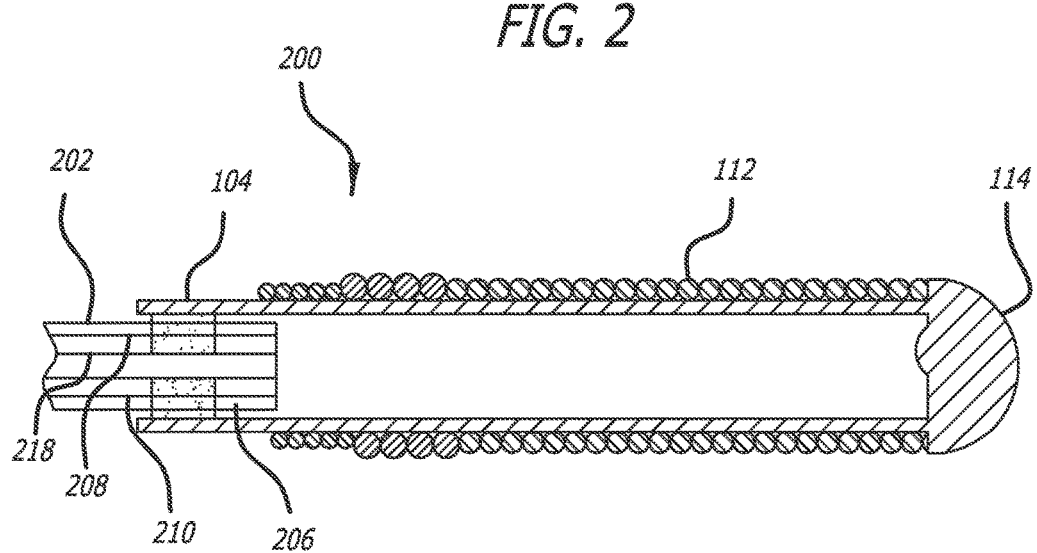
FIG. 2 illustrates a cross-sectional side view of a second embodiment of a detachment system according to the present invention.

Turning to FIG. 2, another embodiment of a detachment system of the present invention, detachment system 200, is illustrated. Detachment system 200 shares several common elements with detachment system 100. For example, the same devices usable as the implant device 112 with detachment system 100 are also usable as the implant device 112 with detachment system 200. These include, e.g., various embolic microcoils and coils. The implant device 112 has been previously described with respect to detachment system 100. As with the implant device 112, the same identification numbers are used to identify other elements/components of detachment system 100 that may correspond to elements/components of detachment system 200. Reference is made to the description of these elements in the description of detachment system 100 as that description also applies to these common elements in detachment system 200.

With detachment system 200, an interior heating element 206 is used to separate a section of a stretch resistant tube 104 and an associated implant device 112 from the detachment system 200. Detachment system 200 includes a delivery pusher 202 that incorporates a core mandrel 218. The detachment system 200 further includes a positive electrical wire 208 and a negative electrical wire 210 that extend through the lumen of the delivery pusher 202.

To form the internal heating element 206, the positive electrical wire 208 and the negative electrical wire 210 may be coupled to the core mandrel 218 of the delivery pusher 202. Preferably, the electrical wires 208, 210 are coupled to a distal portion of the core mandrel 218.

In one embodiment, the positive electrical wire 208 is coupled to a first distal location on the core wire 218, and the negative electrical wire 210 is coupled to a second distal location on the core mandrel 218, with the second distal location being proximal to the first distal location. In another embodiment, the configuration is reversed, i.e., the positive electrical wire 208 is coupled to the second distal location and the negative electrical wire 210 is coupled to the first distal location on the core mandrel 218. When the positive electrical wire 208 and the negative electrical wire 210 are coupled to the distal portion of the core mandrel 218, the distal portion of the core mandrel 218 along with the electrical wires 208, 210 forms a circuit that is the interior heating element 206.

The heater 206 increases in temperature when a current is applied from a power source (not shown) that is coupled to the positive electrical wire 208 and the negative electrical wire 210. As a result, the portion of the stretch resistant tether 104 in proximity to the heater 206 severs and is detached from the detachment system 200 along with the implant device 112.

Because the heater 206 is located within the lumen of the tube-shaped tether 104, the heater 206 is insulated from the body of the patient. As a result, the possibility of inadvertent damage to the surrounding body tissue due to the heating of the heater 206 may be reduced.

In one embodiment of the detachment system 200, the proximal end of the stretch resistant tether 104 (or the distal end of a larger tube (not shown) coupled to the proximal end of the stretch resistant tether 104) may be flared in order to address size constraints and facilitate the assembly of the detachment system 200.

In a similar manner as with detachment system 100, energy may be stored within the system with, for example, an optional compressive spring 116 or by pre-tensioning the tether 104 during assembly as previously described. When present, the release of potential energy stored in the system operates to apply additional pressure to separate the implant device 112, and the portion of the stretch resistant tether 104 to which the implant device 112 is coupled, away from the heater 206 when the implant device 112 is deployed. This advantageously lowers the required detachment time and temperature by causing the tether 104 to sever and break.

As with detachment system 100, the distal end of the stretch resistant tether 104 of detachment system 200 may be tied or coupled to the distal end of the implant device 112, or may be melted or otherwise formed into an atraumatic distal end 114.

FIG. 4 illustrates another preferred embodiment of a detachment system 300. In many respects, the detachment system 300 is similar to the detachment system 200 shown in FIG. 2 and detachment system 100 shown in FIG. 1. For example, the detachment system 300 includes a delivery pusher 301 containing a heater 306 that detaches an implant device 302. Detachment system 300 also utilizes a tether 310 to couple the implant device 302 to the delivery pusher 301.

In the cross-sectional view of FIG. 4, a distal end of the delivery pusher 301 is seen to have a coil-shaped heater 306 that is electrically coupled to electrical wires 308 and 309. These wires 308, 309 are disposed within the delivery pusher 301, exiting at a proximal end of the delivery pusher 301 and coupling to a power supply (not shown). The tether 310 is disposed in proximity to the heater 306, having a proximal end fixed within the delivery pusher 301 and a distal end coupled to the implant device 302. As current is applied through wires 308 and 309, the heater 306 increases in temperature until the tether 310 breaks, releasing the implant device 302.

To reduce the transfer of heat from the heater 306 to the surrounding tissue of the patient and to provide electrical insulation, an insulating cover 304 is included around at least the distal end of the outer surface of the delivery pusher 301. As the thickness of the cover 304 increases, the thermal insulating properties also increase. However, increased thickness also brings increased stiffness and a greater diameter to the delivery pusher 301 that could increase the difficulty of performing a delivery procedure. Thus, the cover 304 is designed with a thickness that provides sufficient thermal insulating properties without overly increasing its stiffness.

To enhance attachment of the tether 310 to the implant device 302, the implant device 302 may include a collar member 322 welded to the implant device 302 at weld 318 and sized to fit within the outer reinforced circumference 312 of the delivery pusher 301. The tether 310 ties around the proximal end of the implant device 302 to form knot 316. Further reinforcement is provided by an adhesive 314 that is disposed around the knot 316 to prevent untying or otherwise unwanted decoupling.

In a similar manner as with detachment systems 100 and 200, energy may be stored within the system with, for example, an optional compressive spring (similar to compressive spring 116 in FIG. 1 but not shown in FIG. 4) or by axially pre-tensioning the tether 104 during assembly. In this embodiment, one end of the tether 310 is attached near the proximal end of the implant device 302 as previously described. The free end of the tether 310 is threaded through a distal portion of the delivery pusher 301 until it reaches an exit point (not shown) of the delivery pusher 301. Tension is applied to the tether 310 in order to store energy in the form of elastic deformation within the tether material by, for example, placing a pre-determined force on the free end of the tether 310 or moving the taut tether 310 a pre-determined displacement. The free end of the tether 310 is then joined to the delivery pusher 301 by, for example, tying a knot, applying adhesive, or similar methods known in the art.

When present, the release of potential energy stored in the system operates to apply additional pressure to separate the implant device 302, and the portion of the tether 310 to which the implant device 302 is coupled, away from the heater 306 when the implant device 302 is deployed. This advantageously lowers the required detachment time and temperature by causing the tether 310 to sever and break.

The present invention also provides for methods of using detachment systems such as detachment systems 100, 200, or 300. The following example relates to the use of detachment system 100, 200, or 300 for occluding cerebral aneurysms. It will, however, be appreciated that modifying the dimensions of the detachment system 100, 200, or 300 and the component parts thereof and/or modifying the implant device 112, 302 configuration will allow the detachment system 100, 200, or 300 to be used to treat a variety of other malformations within a body.

With this particular example, the delivery pusher 102, 202, or 301 of the detachment system 100, 200, or 300 may be approximately 0.010 inches to 0.030 inches in diameter. The tether 104, 310 that is coupled near the distal end of the delivery pusher 102, 202, or 301 and is coupled the implant device 112, 302 may be 0.0002 inches to 0.020 inches in diameter. The implant device 112, 302; which may be a coil, may be approximately 0.005 inches to 0.020 inches in diameter and may be wound from 0.0005 inch to 0.005 inch wire.

If potential energy is stored within the detachment system 100, 200, or 300, the force used to separate the implant device 112, 302 typically ranges up to 250 grams.

The delivery pusher 102, 202, or 301 may comprise a core mandrel 218 and at least one electrically conductive wire 108, 110, 208, 210, 308, or 309. The core mandrel 218 may be used as an electrical conductor, or a pair of conductive wires may be used, or a bipolar wire may be used as previously described.

Figure 8:
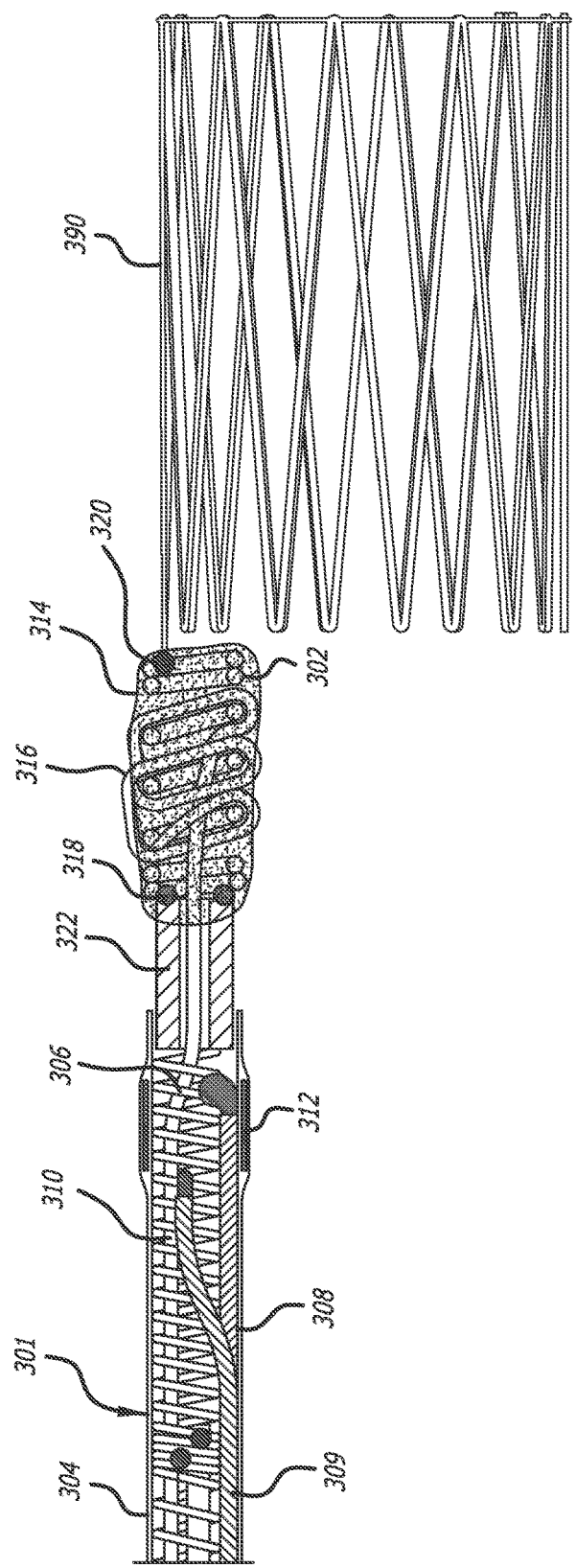
FIG. 8 illustrates a cross-sectional side view of a detachment system including a stent according to the present invention.

Although the detachment systems 100, 200, and 300 have been illustrated as delivering a coil, other implant devices are contemplated in the present invention. For example, FIG. 8 illustrates the detachment system 300 as previously described in FIG. 4 having an implant that is a stent 390. This stent 390 could similarly be detached by a similar method as previously described in regards to the detachment systems 100, 200, and 300. In a further example, the detachment systems 100, 200, or 300 may be used to deliver a filter, mesh, scaffolding or other medical implant suitable for delivery within a patient.

Figure 7:
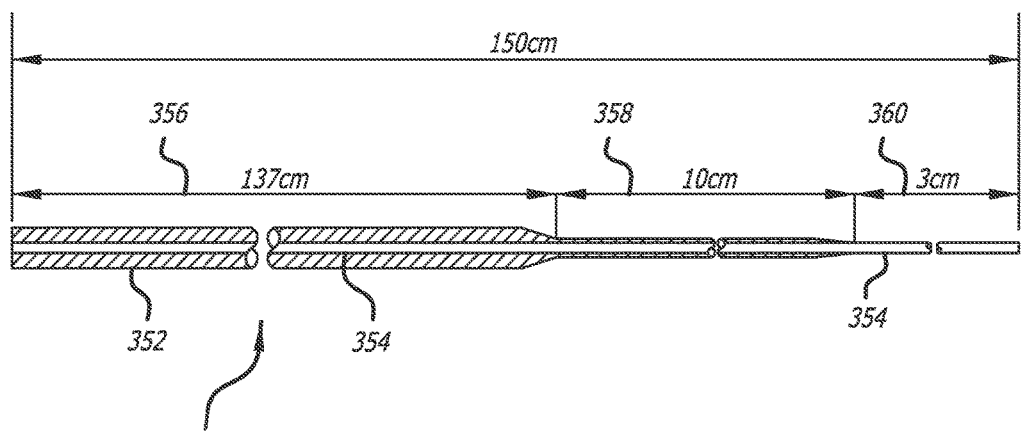
FIG. 7 illustrates a cross-sectional side view of radiopaque layers of a detachment system according to the present invention.

FIG. 7 presents an embodiment of a delivery pusher 350, which could be used in any of the embodiments as delivery pusher 102, 202, or 301, which includes radiopaque materials to communicate the position of the delivery pusher 350 to the user. Specifically, the radiopaque marker material is integrated into the delivery pusher 350 and varied in thickness at a desired location, facilitating easier and more precise manufacturing of the final delivery pusher 350.

Prior delivery pusher designs, such as those seen in U.S. Pat. No. 5,895,385 to Guglielmi, rely on high-density material such as gold, tantalum, tungsten, or platinum in the form of an annular band or coil. The radiopaque marker is then bonded to other, less dense materials, such as stainless steel, to differentiate the radiopaque section. Since the radiopaque marker is a separate element placed at a specified distance (often about 3 cm) from the tip of the delivery pusher, the placement must be exact or the distal tip of the delivery pusher 350 can result in damage to the aneurysm or other complications. For example, the delivery pusher 350 may be overextended from the microcatheter to puncture an aneurysm. Additionally, the manufacturing process to make a prior delivery pusher can be difficult and expensive, especially when bonding dissimilar materials.

The radiopaque system of the present invention overcomes these disadvantages by integrating a first radiopaque material into most of the delivery pusher 350 while varying the thickness of a second radiopaque material, thus eliminating the need to bond multiple sections together. As seen in FIG. 7, the delivery pusher 350 comprises a core mandrel 354 (i.e. the first radiopaque material), preferably made from radiopaque material such as tungsten, tantalum, platinum, or gold (as opposed to the mostly radiolucent materials of the prior art designs such as steel, Nitinol, and Elgiloy).

The delivery pusher 350 also includes a second, outer layer 352, having a different radiopaque level. Preferably, outer layer 352 is composed of a material having a lower radiopaque value than the core mandrel 354, such as Elgiloy, Nitinol, or stainless steel (commercially available from Fort Wayne Metals under the trade name DFT). In this respect, both the core mandrel 354 and the outer layer 352 are visible and distinguishable from each other under fluoroscopy. The outer layer 352 varies in thickness along the length of the delivery pusher 350 to provide increased flexibility and differentiation in radio-density. Thus the thicker regions of the outer layer 352 are more apparent to the user than the thinner regions under fluoroscopy.

The transitions in thickness of the outer layer 352 can be precisely created at desired locations with automated processes such as grinding, drawing, or forging. Such automated processes eliminate the need for hand measuring and placement of markers and further eliminates the need to bond a separate marker element to other radiolucent sections, thus reducing the manufacturing cost and complexity of the system.

In the present embodiment, the delivery pusher 350 includes three main indicator regions of the outer layer 352. A proximal region 356 is the longest of the three at 137 cm, while a middle region 358 is 10 cm and a distal region 360 is 3 cm. The length of each region can be determined based on the use of the delivery pusher 350. For example, the 3 cm distal region 360 may be used during a coil implant procedure, as known in the art, allowing the user to align the proximal edge of the distal region 360 with a radiopaque marker on the microcatheter within which the delivery pusher 350 is positioned. The diameter of each of the regions depends on the application and size of the implant. For a typical cerebral aneurysm application for example, the proximal region 356 may typically measure 0.005-0.015 inches, the middle region 358 may typically measure 0.001-0.008 inches, while the distal region 360 may typically measure 0.0005-0.010 inches. The core mandrel 354 will typically comprise between about 10-80% of the total diameter of the delivery pusher 350 at any point.

Alternately, the delivery pusher 350 may include any number of different regions greater than or less than the three shown in FIG. 7. Additionally, the radiopaque material of the core mandrel 354 may only extend partially through the delivery pusher 350. For example, the radiopaque material could extend from the proximal end of the core mandrel 354 to three centimeters from the distal end of the delivery pusher 350, providing yet another predetermined position marker visible under fluoroscopy.

In this respect, the regions 356, 358, and 360 of delivery pusher 350 provide a more precise radiopaque marking system that is easily manufactured, yet is readily apparent under fluoroscopy. Further, the increased precision of the markers may decrease complications relating to improper positioning of the delivery pusher during a procedure.

In operation, the microcatheter is positioned within a patient so that a distal end of the microcatheter is near a target area or lumen. The delivery pusher 350 is inserted into the proximal end of the microcatheter and the core mandrel 354 and outer layer 352 are viewed under fluoroscopy. The user aligns a radiopaque marker on the microcatheter with the beginning of the distal region 360, which communicates the location of the implant 112, 302 relative to the tip of the microcatheter.

In some situations, for example, small aneurysms where there may be an elevated risk of vessel damage from the stiffness of the delivery pusher 350, the user may position the proximal end of the implant slightly within the distal end of the microcatheter during detachment. The user then may push the proximal end of the implant 112, 302 out of the microcatheter with the next coil, an adjunctive device such as guidewire, or the delivery pusher 102, 202, 301, or 350. In another embodiment, the user may use the radiopaque marking system to locate the distal end of the delivery pusher outside the distal end of the microcatheter.

Once the implant device 112, 302 of the detachment system 100, 200, or 300 is placed in or around the target site, the operator may repeatedly reposition the implant device 112, 302 as necessary or desired.

When detachment of the implant device 112, 302 at the target site is desired, the operator applies energy to the heater 106, 206, or 306 by way of the electrical wires 108, 110, 208, 210, 308, or 309. The electrical power source for the energy may be any suitable source, such as, e.g., a wall outlet, a capacitor, a battery, and the like. For one aspect of this method, electricity with a potential of approximately 1 volt to 100 volts is used to generate a current of 1 milliamp to 5000 milliamps, depending on the resistance of the detachment system 100, 200, or 300.

One embodiment of a connector system 400 that can be used to electrically couple the detachment system 100, 200, or 300 to the power source is shown in FIG. 6. The connector system 400 includes an electrically conductive core mandrel 412 having a proximal end surrounded by an insulating layer 404. Preferably the insulating layer 404 is an insulating sleeve such as a plastic shrink tube of polyolefin, PET, Nylon, PEEK, Teflon, or polyimide. The insulating layer 404 may also be a coating such as polyurethane, silicone, Teflon, paralyene. An electrically conductive band 406 is disposed on top of the insulating layer 404 and secured in place by molding bands 414, adhesive, or epoxy. Thus, the core mandrel 412 and the conductive band 406 are electrically insulated from each other. The conductive band 406 is preferably composed of any electrically conductive material, such as silver, gold, platinum, steel, copper, conductive polymer, conductive adhesive, or similar materials, and can be a band, coil, or foil. Gold is especially preferred as the conductive material of the conductive band 406 because of the ability of gold to be drawn into a thin wall and its ready availability. The core mandrel 412 has been previously described and may be plated with, for example, gold, silver, copper, or aluminum to enhance its electrical conductivity.

The connector system 400 also includes two electrical wires 408 and 410 which connect to the conductive band 406 and core member 412, respectively, and to a heating element at the distal end of a delivery system such as those described in FIGS. 1, 2, and 4 (not shown in FIG. 6). These wires 408 and 410 are preferably connected by soldering, brazing, welding, laser bonding, or conductive adhesive, or similar techniques.

Once the user is ready to release the implant 112, 302 within the patient, a first electrical clip or connector from a power source is connected to a non-insulated section 402 of the core mandrel 412 and a second electrical clip or connector from the power source is connected to the conductive band 406. Electrical power is applied to the first and second electrical clips, forming an electrical circuit within the detachment system 100, 200, or 300, causing the heater 106, 206, or 306 to increase in temperature and sever the tether 104, 310.

Once the detachment system 100, 200, or 300 is connected to the power source the user may apply a voltage or current as previously described. This causes the heater 106, 206, or 306 to increase in temperature. When heated, the pre-tensioned tether 104, 310 will tend to recover to its unstressed (shorter) length due to heat-induced creep. In this respect, when the tether 104, 310 is heated by the heater 106, 206, or 306; its overall size shrinks. However, since each end of the tether 104, 310 is fixed in place as previously described, the tether 104, 310 is unable to shorten in length, ultimately breaking to release the implant device 112, 302.

Because there is tension already within the system in the form of a spring 116 or deformation of the tether material 104, 310; the amount of shrinkage required to break the tether 104, 310 is less than that of a system without a pre-tensioned tether. Thus, the temperature and time required to free the implant device 112, 302 is lower.

Figure 5:
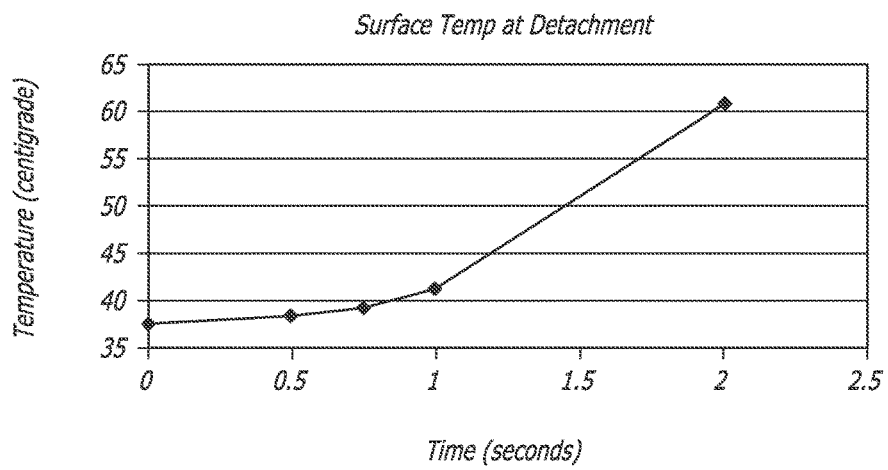
FIG. 5 illustrates example temperature data of the surface of a detachment system according to the present invention.

FIG. 5 is a graph showing the temperatures at the surface of PET cover 304 of the detachment system 300. As can be seen, the surface temperature of the detachment system 300 during detachment does not vary linearly with time. Specifically, it only takes just under 1 second for the heat generated by the heating coil 306 to penetrate the insulating cover 304. After 1 second, the surface temperature of the insulating cover 304 dramatically increases. Although different outer insulating material may slightly increase or decrease this 1-second surface temperature window, the necessarily small diameter of the detachment system 100, 200, or 300 prevents providing a thick insulating layer that may more significantly delay a surface temperature increase.

It should be understood that the embodiments of the detachment system 100, 200, or 300 include a variety of possible constructions. For example, the insulating cover 304 may be composed of Teflon, PET, polyamide, polyimide, silicone, polyurethane, PEEK, or materials with similar characteristics. In the embodiments 100, 200, or 300 the typical thickness of the insulating cover is 0.0001-0.040 inches. This thickness will tend to increase when the device is adapted for use in, for example, proximal malformations, and decrease when the device is adapted for use in more distal, tortuous locations such as, for example, cerebral aneurysms.

In order to minimize the damage and possible complications caused by such a surface temperature increase, the present invention detaches the implant device 112, 302 before the surface temperature begins to significantly increase. Preferably, the implant device 112, 302 is detached in less than a second, and more preferably, in less than 0.75 seconds. This prevents the surface temperature from exceeding 50° C. (122° F.), and more preferably, from exceeding 42° C. (107° F.).

Once the user attempts to detach the implant device 112, 302, it is often necessary to confirm that the detachment has been successful. The circuitry integrated into the power source may be used to determine whether or not the detachment has been successful. In one embodiment of the present invention an initial signaling current is provided prior to applying a detachment current (i.e. current to activate the heater 106, 206, or 306 to detach an implant 112, 302). The signaling current is used to determine the inductance in the system before the user attempts to detach the implant and therefore has a lower value than the detachment current, so as not to cause premature detachment. After an attempted detachment, a similar signaling current is used to determine a second inductance value that is compared to the initial inductance value. A substantial difference between the initial inductance and the second inductance value indicates that the implant 112, 302 has successfully been detached, while the absence of such a difference indicates unsuccessful detachment. In this respect, the user can easily determine if the implant 112, 302 has been detached, even for delivery systems that utilize nonconductive temperature sensitive polymers to attach an implant, such as those seen in FIGS. 1, 2, and 4.

In the following description and examples, the terms "current" and "electrical current" are used in the most general sense and are understood to encompass alternating current (AC), direct current (DC), and radiofrequency current (RF) unless otherwise noted. The term "changing" is defined as any change in current with a frequency above zero, including both high frequency and low frequency. When a value is measured, calculated and/or saved, it is understood that this may be done either manually or by any known electronic method including, but not limited to, an electronic circuit, semiconductor, EPROM, computer chip, computer memory such as RAM, ROM, or flash; and the like. Finally, wire windings and toroid shapes carry a broad meaning and include a variety of geometries such as circular, elliptical, spherical, quadrilateral, triangular, and trapezoidal shapes.

When a changing current passes through such objects as wire windings or a toroid, it sets up a magnetic field. As the current increases or decreases, the magnetic field strength increase or decreases in the same way. This fluctuation of the magnetic field causes an effect known as inductance, which tends to oppose any further change in current. Inductance (L) in a coil wound around a core is dependant on the number of turns (N), the cross-sectional area of the core (A), the magnetic permeability of the core (μ), and length of the coil (l) according to Equation 1 below:

$$L = \frac{.4\pi N^2 A \mu}{l} \qquad \text{Equation 1}$$

Figure 3A:
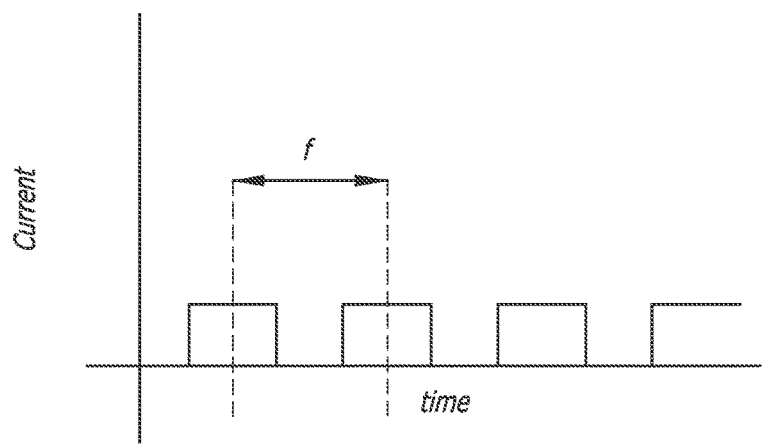
FIG. 3A illustrates example direct signaling current according to the present invention.
Figure 3B:
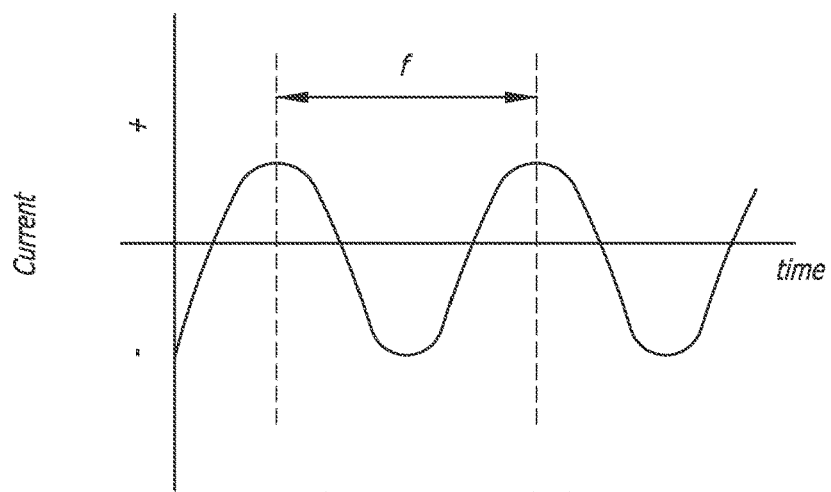
FIG. 3B illustrates example alternating signaling current according to the present invention.

The heater 106 or 306 is formed from a wound coil with proximal and distal electrically conductive wires 108, 110, 308, or 309 attached to a power source. The tether 104, 310 has a magnetic permeability μ1 and is positioned through the center of the resistive heater, having a length l, cross sectional area A, and N winds, forming a core as described in the previous equation. Prior to detachment, a changing signaling current i1, such as the waveforms shown in FIGS. 3A and 3B, with frequency f1, is sent through the coil windings. This signaling current is generally insufficient to detach the implant. Based on the signaling current, the inductive resistance XL (i.e. the electrical resistance due to the inductance within the system) is measured by an electronic circuit such as an ohmmeter. The initial inductance of the system L1 is then calculated according to the formula:

$$L_1 = \frac{X_L}{2\pi f_1} \qquad \text{Equation 2}$$

This initial value of the inductance L1 depends on the magnetic permeability μ1 of the core of the tether 104, 310 according to Equation 1, and is saved for reference. When detachment is desired, a higher current and/or a current with a different frequency than the signaling current is applied through the resistive heater coil, causing the tether 104, 310 to release the implant 112, 302 as previously described. If detachment is successful, the tether 104, 310 will no longer be present within the heater 106, 306 and the inside of the heater 106, 306 will fill with another material such as the patient's blood, contrast media, saline solution, or air. This material now within the heater core will have a magnetic permeability µ2 that is different than the tether core magnetic permeability µ1.

A second signaling current and frequency f2 is sent through the heater 106, 306 and is preferably the same as the first signaling current and frequency, although one or both may be different without affecting the operation of the system. Based on the second signaling current, a second inductance L2 is calculated. If the detachment was successful, the second inductance L2 will be different (higher or lower) than the first inductance L1 due to the difference in the core magnetic permeabilities µ1 and µ2. If the detachment was unsuccessful, the inductance values should remain relatively similar (with some tolerance for measurement error). Once detachment has been confirmed by comparing the difference between the two inductances, an alarm or signal can be activated to communicate successful detachment to the user. For example, the alarm might include a beep or an indicator light.

Preferably, the delivery system 100, 300 used according to this invention connects to a device that automatically measures inductance at desired times, performs required calculations, and signals to the user when the implant device has detached from the delivery catheter. However, it should be understood that part or all of these steps can be manually performed to achieve the same result.

The inductance between the attached and detached states can also preferably be determined without directly calculating the inductance. For example, the inductive resistance XL can be measured and compared before and after detachment. In another example, the detachment can be determined by measuring and comparing the time constant of the system, which is the time required for the current to reach a predetermined percentage of its nominal value. Since the time constant depends on the inductance, a change in the time constant would similarly indicate a change in inductance.

The present invention may also include a feedback algorithm that is used in conjunction with the detachment detection described above. For example, the algorithm automatically increases the detachment voltage or current automatically after the prior attempt fails to detach the implant device. This cycle of measurement, attempted detachment, measurement, and increased detachment voltage/current continues until detachment is detected or a predetermined current or voltage limit is attained. In this respect, a low power detachment could be first attempted, followed automatically by increased power or time until detachment has occurred. Thus, battery life for a mechanism providing the detachment power is increased while the average coil detachment time is greatly reduced.

Figure 9:
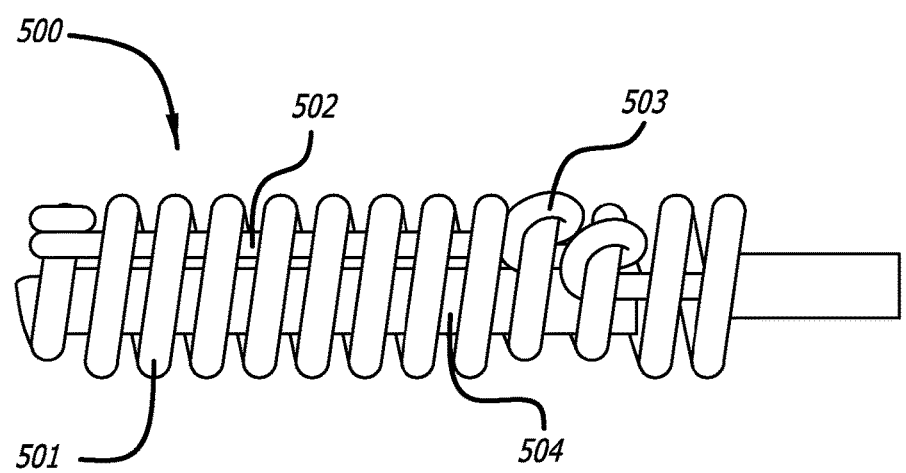
FIG. 9 illustrates a side elevation view of an embodiment of an implant according to the present invention.

Referring now to FIG. 9, there is shown an embodiment of an implant 500 of the present invention. In one embodiment, the implant 500 includes a coil 501 and a stretch-resistant member 502, the stretch-resistant member 502 being configured to form a wrap or knot 503 about at least one wind of said coil 501.

The coil 501 of an implant 500 may be formed from winds of, for example, metal or plastic wire. Although shown in a straight configuration in FIG. 9, a coil may also be formed into a different configuration, such as a helical wind, flower shape, sphere, box or similar complex shape (not shown).

The stretch-resistant member 502 of an implant 500 may be formed from a variety of materials such as polyolefin, polyethylene, polyolefin elastomers such as ethylene-octene copolymer, biodegradable materials such as PGLA, hydrogel materials based on, for example, acrylamide or polyethylene glycol (PEG), polyethylene terephthalate (PET), Nylon or amide-based polymers or block copolymers such as PEBAX, polypropylene, etc.

The stretch-resistant member 502 has a distal end and a proximal end and runs through the interior lumen of the coil 501 and, preferably, exits the winds of the coil 501 near the proximal end of the coil 501. The stretch-resistant member 502 is then configured to wrap or tie around one or more winds of the coil 501 near the proximal end of the coil 501. The stretch-resistant member 502 is then preferably attached near the distal end of a coil 501 by wrapping or tying a knot (503, as shown in FIG. 9), adhesive bonding, melting the end of the stretch-resistant member 502 to form a ball, or a combination of the methods. In the embodiment in which a wrap or knot 503 is employed, the wrap or knot 503 may be made formed from a variety of techniques including an overhand knot, a half stitch, a surgeon's knot, or a combination of wraps and knots. In a preferred embodiment, the stretch-resistant member 502 is configured such that it does not wrap around itself. In such a configuration, the tensile strength of the stretch-resistant member 502 is increased.

Once a wrap or knot 503 is formed, a free (proximal) end of the stretch-resistant member 502 remains. At this point in the manufacturing process, the portion of the member 502 distal to the wrap or knot 503 up to the distal attachment point will provide stretch resistance to the proximal end of the member because the knot or wrap 503 (along with any adhesive used) is configured to reduce or prevent slipping. Thus, the coil 501 will substantially retain its original configuration as formed prior to introduction of the stretch-resistant member 502.

The proximal end of the stretch-resistant member 502 is then passed through, around and/or in proximity to a heater element and tension is then placed on the proximal portion of the stretch-resistant member 502 as described in U.S. patent Ser. No. 11/212,830 (as earlier described and incorporated by reference herein). Since the distal portion of the stretch-resistant member 502 is at least partially isolated from the proximal portion of the stretch-resistant member 502 by the wrap or knot 503, the tension in the distal portion of the stretch-resistant member 502 that is distal to the wrap or knot 503 will be less than the tension in the proximal portion of the stretch-resistant member 502 that is proximal to the wrap or knot 503. The proximal end or a proximal segment of the stretch-resistant member 502 is then tied, bonded or otherwise attached to the delivery catheter.

The implant 500 is then introduced into a body and positioned by methods known in the art. When the implant has been placed in the desired position (e.g., where the user intends to detach it from a delivery catheter), the heating element is activated as described in U.S. patent application Ser. No. 11/212,830 and the member 502 is severed at or near the heater element. Thus, in one embodiment, the distal end of the member 502 remains bonded to the implant 500 and the proximal end of the member 502 remains bonded to the delivery catheter after the coil 501 is detached.

As shown in FIG. 9, a preferred embodiment of the present invention includes a hydrogel material 504, which may be placed in proximity to the stretch-resistant member 502. In FIG. 9, the hydrogel material runs substantially parallel to the stretch-resistant member 502. In another embodiment, the hydrogel material may be wrapped, tied around or otherwise intertwined with the stretch-resistant member and/or the coil (not shown).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A detachable implant delivery system, comprising:
   a delivery device having a heater coil proximate a distal end of said delivery device;
   a microcoil comprising a helical wire; and,
   a stretch-resistant member characterized by a single monofilament and connecting said delivery device and said microcoil; said stretch-resistant member passing through a lumen of said microcoil and being attached at a first location near a distal end of said microcoil, at a second location near a proximal end of said microcoil, and at a third location near a distal end of said delivery device, such that said stretch-resistant member is located within said heater coil;
   wherein a first portion of said stretch-resistant member is between said second location and said third location is tensioned so as to enhance breakage upon application of heat by said heater coil, and wherein a second portion of said stretch-resistant member is isolated from the tension of said first portion so as to resist stretching and thereby retain an original configuration of said microcoil.

2. The detachable implant delivery system of claim 1, wherein said stretch-resistant member is attached to said microcoil at said first location with a knot.

3. The detachable implant delivery system of claim 1, wherein said stretch-resistant member is attached to said microcoil at said first location with adhesive bonding.

4. The detachable implant delivery system of claim 1, wherein said stretch-resistant member comprises a material selected from the group consisting of polyolefin, polyethylene, polyolefin elastomers, ethylene-octene copolymer, biodegradable materials, PGLA, hydrogel, acrylamide, PEG, PET, nylon, amide-based polymers, block copolymers, PEBAX, polypropylene.

5. The detachable implant delivery system of claim 1, wherein said microcoil further comprises a hydrogel material.

6. The detachable implant delivery system of claim 1, wherein said second section of said stretch-resistant member is connected at said distal location of said microcoil by melting said tether to form a ball.

7. A method of detaching a microcoil from an implant delivery system, comprising:
   advancing a delivery system within a patient;
   activating a heater located at a distal end of said implant delivery system;
   heating a first section of a tether that is pre-tensioned between a first location on said implant delivery device so as to enhance breakage along said first section of said tether; said tether further connecting to a second location at a proximal end of said microcoil so as form a second section;
   breaking said tether along said first section so as to release tension between said first location and said second location;
   maintaining connection of said second section of said tether at said second location and at a third location at a distal end of said microcoil; said second section being isolated from changes in tension between said first location and said second location so as to resist stretching to retain an original configuration of said microcoil.

8. The method of claim 7, wherein said tether comprises a material selected from the group consisting of polyolefin, polyethylene, polyolefin elastomers, ethylene-octene copolymer, biodegradable materials, PGLA, hydrogel, acrylamide, PEG, PET, nylon, amide-based polymers, block copolymers, PEBAX, polypropylene.

9. The method of claim 7, wherein said tether is tied with a knot at said third location.

10. The method of claim 7, wherein said tether is connected at said distal end of said microcoil by melting said tether to form a ball.

* * * * *